(12) United States Patent
van Dongen et al.

(10) Patent No.: US 6,730,474 B1
(45) Date of Patent: May 4, 2004

(54) MOLECULAR DETECTION OF CHROMOSOME ABERRATIONS

(75) Inventors: Jacobus Johannus Maria van Dongen, Nieuwerker aan de IJssel (NL); Anthonie Willem Langerak, Barendrecht (NL)

(73) Assignee: Erasmus Universiteit Rotterdam, Rotterdam (NL)

( * ) Notice: Subject to any disclaimer, the term of this patent is extended or adjusted under 35 U.S.C. 154(b) by 0 days.

(21) Appl. No.: 09/439,040

(22) Filed: Nov. 12, 1999

Related U.S. Application Data

(63) Continuation of application No. PCT/NL98/00270, filed on May 13, 1998.

(30) Foreign Application Priority Data

May 13, 1997 (EP) ............................................ 97201440

(51) Int. Cl.[7] .......................... C12Q 1/68; C07H 21/04; C07H 19/04; C12P 19/34
(52) U.S. Cl. ...................... 435/6; 435/91.1; 536/23.1; 536/24.3; 536/25.32; 536/26.6
(58) Field of Search .................... 435/6, 91.1, 91.2, 435/810; 536/23.1, 24.3, 25.32, 26.6, 24.2, 24.31, 23.5

(56) References Cited

U.S. PATENT DOCUMENTS

| | | | |
|---|---|---|---|
| 5,487,970 A | * 1/1996 | Rowley et al. | ................. 435/6 |
| 5,538,869 A | 7/1996 | Siciliano et al. | |
| 5,567,586 A | * 10/1996 | Croce | ............................ 435/6 |

FOREIGN PATENT DOCUMENTS

| | | |
|---|---|---|
| EP | 0 430 402 A2 | 6/1991 |
| EP | 0 500 290 A2 | 8/1992 |
| WO | WO 94/24308 | * 10/1994 |
| WO | WO 96/17958 | 6/1996 |
| WO | WO 98/51817 | 11/1998 |

OTHER PUBLICATIONS

Tkachuk et al. Detection of bcr–abl fusion in chronic myelogeneous leukemia by in situ hydridization. Science .vol. 250, pp. 559–562.*

Tkachuk et al. Detection of bcr–abl fusion in chronic myelogeneous leukemia by in situ hybridization. Science .vol. 250, pp. 559–562, Oct. 1990.* du Manoir et al., "Detection of complete and partial chromosome gains and losses by comparative genomic in situ hybridization", *Human Genetics*, 90:590–610; 1993.

Thompson et al., Cytogenetic Profiling Using Fluorescence In Situ Hybridization (FISH) and Comparative Genomic Hybridization (CGH), *Journal of Cellular Biochemistry*, 17G:139–143 (1993).

Tkachuk et al., "Clinical Applications of Fluorescence in situ Hybridization", *Genetic Analysis Techniques and Applications*, 8(2):67–74, 1991.

Tkachuk et al., "Detection of bcr–abl Fusion in Chronic Myelogeneous Leukemia by in Situ Hybridization", *Science*, pp. 559–562, Oct. 26, 1990.

* cited by examiner

*Primary Examiner*—Kenneth R. Horlick
*Assistant Examiner*—Cynthia Wilder
(74) *Attorney, Agent, or Firm*—TraskBritt

(57) ABSTRACT

The invention relates to the field of cytogenetics and the application of genetic diagnostic techniques in pathology and hematology. Specifically, the invention relates to nucleic acid probes that can be used in hybridization techniques for the detection of chromosomal aberrations and other gene rearrangements such as immunoglobulin and T cell receptor gene rearrangements. The probes provided by the invention are a distinct and balanced set of probes of comparable size each preferably being from 1 to 100 kb, or smaller, and flanking a potential breakpoint in a chromosome.

10 Claims, No Drawings

MOLECULAR DETECTION OF CHROMOSOME ABERRATIONS

CROSS REFERENCE TO RELATED APPLICATION

This application is a continuation of pending International Application No. PCT/NL98/00270, filed on May 13, 1998 designating the United States of America, which itself claims priority from EP 97201440.1 filed on May 13, 1997.

TECHNICAL FIELD

The invention relates to the field of cytogenetics and the application of genetic diagnostic techniques in pathology and hematology. Specifically, the invention relates to nucleic acid probes that can be used in hybridization techniques for the detection of chromosomal aberrations and other gene rearrangements such as immunoglobulin (Ig) and T cell receptor (TCR) gene rearrangements.

BACKGROUND

Chromosomal aberrations are a leading cause of genetic disorders or diseases, including congenital disorders and acquired diseases such as malignancies. At the base of these malignancies is the fact that all cells of a malignancy have a common clonal origin. Chromosomal aberrations in malignancies stem from rearrangements, translocations, inversions, insertions, deletions and other mutations of chromosomes, but also losses or gains of whole chromosomes are found in malignancies. In many chromosome aberrations, two different chromosomes are involved. In this way, genes (or fragments of genes) are removed from the normal physiological context of a particular chromosome and are located to a recipient chromosome, adjacent to non-related genes or fragments of genes (often oncogenes or proto-oncogenes). Such an aberrant genetic combination can be the foundation of a malignancy.

Often, such rearrangements involving two non-aberrant chromosomes happen in a somewhat established pattern. Breaks occur in either of the two chromosomes at a potential breakpoint or breakpoint cluster region resulting in removal of a gene or gene fragment from one chromosome and subsequent translocation to the other chromosome thereby forming a rearranged chromosome where the rearranged fragments are fused in a fusion region.

Detection of chromosome aberrations can be achieved using a wide array of techniques, various of which entail modern biomolecular technology. Traditional techniques such as cytogenetic analyses by conventional chromosome banding techniques are, although highly precise, very labor intensive, require skilled personal and are expensive. Automated karyotyping is useful for some diagnostic applications, such as prenatal diagnosis, but is ineffective in analyzing the complex chromosomal aberrations of many malignancies. Furthermore, above techniques require fresh (cultured) cells, which are not always available.

Other, more modern, techniques are Southern blotting or other nucleic acid hybridization techniques or amplification techniques such as polymerase chain reaction ("PCR"), for the detection of well-defined chromosome aberrations for which suitable nucleic acid probes or primers are available. With these techniques, fresh or frozen cells can be used, and sometimes even samples after formalin fixation as long as the nucleic acid sequences to be hybridize or amplified remain intact and accessible. However, even with this modern technology, several disadvantages can be found that hamper the application of these diagnostic techniques in the rapid screening for chromosomal aberrations related to said malignancies.

Southern blotting lasts 3 to 4 weeks, which is too slow for efficient diagnosis and choice of therapy in malignancies, and allows only 10–15 kb of nucleic acid sequences to be analyzed per probe analysis.

PCR, although, in essence, well-suited for rapid and massive diagnostic testing or even screening, allows only 0.1 to 2 kb of nucleic acid to be analyzed per PCR analysis, which greatly hampers rapid screening of vast stretches of chromosomes and breakpoint cluster regions within the chromosomes. An additional disadvantage of PCR is its inherent sensibility to mismatched primers. Small normal, and physiological alterations which can always be present in the nucleic acid sequence of the gene fragment complementary to the primer hamper the reliable application of PCR and eventually give rise to false-negative results. Especially false-negative results render a PCR-based diagnostic test, albeit very specific, not sensitive enough for reliable diagnosis, and it goes without saying that only a reliable diagnosis of malignancies can contribute to an understanding of the prognosis and the design of an adequate therapy.

Fluorescent in situ hybridization ("FISH") techniques are less dependent on the complete matching of nucleic acid sequences to get positive diagnostic results. In general, FISH employs probe analyses with large, mainly unspecified, nucleic acid probes that hybridize however often with varying stringency, with the genes or gene fragments located at both sides of the fusion region in the rearranged chromosome in the malignant cell. Using large probes renders the FISH technique very sensitive. The binding of the co-locaizing probes is generally detected either directly or indirectly with fluorochromes and visualized via fluorescence microscopy of a population of cells obtained from the sample to be tested.

However, even the currently used FISH protocols have inherent disadvantages. These disadvantages mainly relate to the selection of nucleic acid probes employed in the current FISH protocols, which can give false-positive results in the diagnosis of chromosomal aberrations. For example, probes directed against different chromosomes with juxtaposition of signals in case of translocation create a rather large risk of false-positive results. Hence, the diagnostic tests, although sensitive, are not specific enough to employ standard FISH techniques in massive or rapid diagnostic testing, let alone in automated testing or screening.

Thus far, generally large probes, derived of cosmic clones, YAC clones, or other cloned DNA fragments have been used as probes in FISH. The exact position of these probes in relation to the fusion region in the rearranged chromosome is unknown and they are of largely unspecified and varying genomic length (genomic length or distance as expressed as the number of nucleotides or bases (b)) and go without specific selection or modification of these probes beyond the mere labeling of the probes with the necessary reporter molecules i.e., fluorochromes. For designing or selecting probes, little or no guidance is given in the art, beyond mere suggestions as to where to localise a putative probe. False-positive results obtained with these probes may stem from a specific hybridization with a wide array of (major) repetitive sequences present throughout various chromosomes, or from cross-hybridization to homologous sequences in the genome, or from overlap of the used probes with the breakpoint cluster region or from the difference in signal intensities as far as originating from size differences of the probes. These causes of false-positive results are frequently not recognized. False-positive results are especially detrimental to rapid diagnosis if rapid or routine screening of patients is needed to detect malignancies or in evaluating treatment protocols. A false-positive result then necessitates cumbersome re-testing of patients, or even unsuspecting clients that have been submitted to routine screening protocols, and can greatly alarm these people. Furthermore, translocations are generally detected with two different probes, one for each of the involved chromosomes, which probes then co-localize during the in situ hybridization in case of a translocation, but show separate signals when no translocation is present (see, e.g., European patent applications EP 0430402 and EP 0500290; Tkachuk et al., *Science* 250:559–562 (1990); Tkachuk et al., "Clinical applications of fluorescence in situ hybridization", *Genetic analysis techniques and applications* 8:67–74 (1991). However, in practice, 2 to 4% of normal interphase cells tested by FISH will show false-positive results due to the fact that the two probes colocalize by chance. An additional disadvantage of the current FISH protocols is that it is in practice necessary to know both chromosomes that are involved in the translocation as well as the relevant breakpoint regions of both chromosomes to the nucleic acid probes enabling the detection of the specified translocation, while as yet unknown or ill-defined translocations originating from a well-known gene and an unknown partner gene remain undetected.

DISCLOSURE OF THE INVENTION

The present invention provides nucleic acid probes that can be used in diagnostic testing for chromosome aberrations which combine a high sensitivity and a high specificity. specificty. The probes provided by the invention can hybridize, in situ or in vivo or in vitro with complementary nucleic acid molecules such as (m)RNA or DNA, as, for example, transcribed by or found in (non-aberrant and/or rearranged) chromosomes.

The present invention provides for each translocation analysis a distinct and balanced pair of nucleic acid probes. The probes are distinct in that they each hybridize to a different sequence specifically selected and flanking a distinct potential breakpoint in a non-aberrant chromosome. Furthermore, the pair formed by, for example, probe A and probe B is distinct from the pair formed by for example, probe A and probe X. Furthermore, in the above example, probes A, B and X constitute three pairs, A-B, B-X and A-X. The probes in the pair are comparable or balanced in that they are designed to be of for example comparable size or genomic length with the final aim of facilitating the generation of signals of comparable intensity. In addition, the probes can be comparably labelled with reporter molecules resulting in signals of comparable intensity. Also, the probes can each be labelled with a different fluorochrome, facilitating detection on one spot of different colour when they co-localize when no aberration is detected. Also, the probes can be selected to react with a chromosome, at respective complementary hybridization sites that are located at comparable distances at each side of a breakpoint or breakpoint cluster region of a chromosome. The distinct and balanced pair of nucleic acid probes provided by the invention entails probes that are for example of comparable size or genomic length, each probe of the pair for example being from 1 to 10 kb, or 7 to 15 kb, or 10 to 20 kb, or 15 to 30 kb, or 20 to 40 kb, or 30 to 50 kb, or 40 to 60 kb, or 50 to 70 kb, or 60 to 80 kb, or 70 to 90 kb, or 80 to 100 kb in length. By using such a distinct and balanced pair of probes flanking a breakpoint region and not overlapping the corresponding fusion region, false-positive diagnosis in hybridization studies is avoided. The invention further provides a distinct and balanced pair of nucleic acid probes, each being labeled with at least one different reporter molecule. Nucleic acid probes can be labeled with chromophores or fluorochromes (e.g., FITC or TRITC) or by introducing a hapen such as biotin and digoxigenin. Fluorochrome labeled probes can be detected directly. Hybridization with haptenised nucleic acid probes is followed by indirect detection using chromopores, florochromes or enzymes such as peroxidase.

The invention further provide a distinct and balanced pair of nucleic acid probes characterized in that both probes hybridize to a single corresponding nucleic acid molecule or its complementary strand, or hybridise to one (non-aberrant) chromosome, hybridize to a fragment thereof, possibly comprising the aberration, instead of two probes that hybridize separately to the two chromosomes that are involved in a given translocation, as currently used in hematology and oncology in general (see, e.g., Tkachuk et al., *Science* 250:559–562, (1990); Tkachuk et al., "Clinical applications of fluorescence in situ hybridization", *Genetic analysis techniques and applications*, vol. 8, 67–74, (1991)).

The inyention further provides a distinct and balanced pair of nucleic acid probes which hybridize to the acid molecule at a genomic distance of no more than 100 kb, but preferably no more than 50 kb. In addition, the invention provides a distinct and balanced pair of nucleic acid probes which hybridize in situ and can i.e., be used in diagnostic tests entailing FISH techniques. Furthermore, the invention provides a distinct and balanced pair of nucleic acid probes which probes each hybridize in situ under varying but generally low stringent conditions to only a few DNA molecules per cell. The nucleic acid probes composed of several DNA fragments are tested either on metaphase spreads or with Southern blotting for hybridization sensitivity and specificity to select the probe on containing as little major repetitive sequences as possible, to avoid high background staining. The nucleic acid probes are tested in fiber FISH (i.e., hybridization on extended single DNA fibers immobilized on glass slides), prior to being employed in diagnostic testing, for mapping and checking their relative positions.

The probes are tested, for example, to avoid using probes hybridizing two repetitive sequences. Probes can consist of sets of various oligonucleotides, thereby avoiding reptitive sequences present in a flanking region. Such sets are distinctly labelled, with separate or distinct reporter molecules for each probe (or set of oligonucleotides) that is aimed at the respective flanking region probes can each consist of multiple labelled oligonucleotides, each hybridizing distinct area in a flanking region. One probe can for example contain from 10 up to 200 of such oligonucleotides, preferably from 50–150, each oligonucleotide for example being 10–20 nucleotides long. For example, the intron-exon structure of the MLL gene is described in the *Br J Haematol*, 93:966–972 (1996). The manuscript also shows that most breakpoints in the MLL gene are located between exon 9 and exon 14. PNA containing probes can be designed in exon 3 to 8 for the "upstream FISH probe" and in exon 15 to 31 for the "downstream FISH probe". Particularly exon 4 and exon 28 are important for probe design, because these two exons are rather large and therefore can contain most of the PNA probes. PNA oligonucleotides can be synthesized for example for their capacity to hybridize with the exon 4 or exon 28 from the 119Q3 target gene and used in one cocktail as probe for one flanking region.

The invention further provides the use of the distinct and balanced pair of probes in diagnostic testing for chromosomal aberrations. The pair of probes according to the invention can be used in the detection of nucleic acid comprising the aberration or fragments of the aberration, or in the detection of cells, in situ or in vitro, comprising the chromosome aberration. The invention thus provides a pair or pairs of distinct and balanced probes which can be used in the detection of disorders or diseases related to chromosomal aberrations, i.e., malignancies, such as haematopoietic malignancies as further explained below. Furthermore, the invention provides a diagnostic kit or assay comprising a pair of nucleic acid probes according to the invention which can be used in the detection of disorders or diseases related to chromosomal aberrations, i.e., malignancies, such as haematopoietic malignancies with such a diagnostic kit or assay provided by the invention it is, for example, possible to monitor the effects of therapy and detect minimal residual disease or detect early relapse of cancer. One can also identify the origin of bone marrow cells following bone marrow transplantation. One can also detect viral sequences, and their localisation in the chromosome, in cells. More in detail the present invention is described while referring to molecular detection of chromosome aberrations in hematopoietic malignancies but is widely applicable for analysis of chromosome aberrations in general.

The development of reliable probes for detection of well-defined or even ill-defined chromosome aberrations in hematological malignancies is described as non-limiting example to illustrate the invention. Such probes can be used for diagnosis and for molecular classification of the involved malignancies. The new probes can be used in diagnostic testing in several types of hematological malignancies with increased sensitivity, specificity, and efficacy of analysis.

BEST MODE OF THE INVENTION

Each year world-wide many cases of hematopoietic malignancies are being diagnosed. In the European Union (~375 million inhabitants) this concerns ~98,000 patients per year. The estimated number of patients in the USA (~250 million inhabitants) is ~65,500 per year. The majority of hematological malignancies are of lymphoid origin: acute lymphoblastic leukemias ("ALL"), chronic lymphocytic leukemias, most malignant lymphomas, and multiple myelomas. The non-Hodgkin's lymphomas ("NHL") form the largest group, representing approximately half of all hematopoietic malignancies. Furthermore, European epidemiological studies show that the incidence of NHL is gradually increasing (~5% per year), which indicates that NHL poses a significant public health problem in Europe and most probably throughout the Western world. Although the annual number of patients diagnosed with ALL is smaller than for NHL, ALL has a high prevalence in children, representing the most frequent malignancy in childhood.

Lymphoid malignancies consist of a broad range of ~25 different disease entities, which differ in clinical presentation, prognosis, and treatment protocols. These disease entities have been defined in the recent Revised European American Lymphoid neoplasm ("REAL") classification. In this classification the lymphoid malignancies are divided in B-cell malignancies (~90%) and T-cell malignancies (~10%).

The diagnosis and classification of lymphoid malignancies is generally based on cytomorphology and histomorphology, complemented with immunophenotypic information via flow cytometry and/or immunohistochemistry. This immunophenotypic information appears to be valuable for classification of lymphoid malignancies, such as the classification of ALL into pro-B-ALL, common-ALL, pre-B-ALL, and several types of T-ALL. In mature B-cell malignancies with immunoglobulin (Ig) expression the diagnosis can be supported by immunophenotypic clonality assessment via detection of single Ig light chain expression, i.e., the distribution of Igκ and Igλ positive B-cells, which is heavily skewed in case of a B-cell malignancy.

The value of clonality assessment is based on the fact that all cells of a malignancy have a common clonal origin. In lymphoid malignancies, this is reflected by the presence of identically (clonally) rearranged Ig and T cell receptor ("TCR") genes: clonal Ig and/or TCR gene rearrangements are found in most (90–95%) immature lymphoid malignancies and virtually all (>98%) mature lymphoid malignancies. Therefore molecular clonality analysis of Ig and TCR genes is highly suitable for discrimination between monoclonal (malignant) and polyclonal (reactive) lymphoproliferations. Suspect lymphoproliferations should therefore be subjected to molecular clonality assessment.

During the last decade the knowledge about genetic aberrations in hematopoietic malignancies has considerably increased, especially in acute leukemias and NHL. Currently, well-established chromosome aberrations are found in 35–40% of ALL and in 30–40% of NHL. These chromosome aberrations can be used as alternative or additional markers for molecular clonality assessment. More importantly, these chromosome aberrations appear to be relevant classification markers, which supplement the currently used morphological and immunophenotypic classification systems. It has been clearly demonstrated that several genetic aberrations are associated with a favorable prognosis, whereas others are associated with poor prognosis, such as t(4;11) in pro-B-ALL and t(9;22) in common-ALL. Several treatment protocols have started to use this information for stratification of treatment. Therefore, it can be anticipated that rapid and reliable detection of well-defined genetic aberrations will become essential in the diagnosis and management of hematopoietic malignancies.

Several different types of chromosome aberrations have been identified in ALL and NHL. The chromosome aberrations in precursor-B-ALL mainly concern translocations, which result in fusion genes, encoding for fusion proteins with new or modified functions. Examples include the E2A-PBX and BCR-ABL fusion proteins, resulting from t(1;19) and t(9;22), respectively. Another important chromosome region, the 11q23 region with the MLL gene, is involved in several types of translocations in acute leukemias. In these 11q23 translocations different partner genes are involved, leading to different fusion proteins. One of them is t(4;11), which is observed in ~700% of infant acute leukemias. Many chromosome aberrations in T-ALL and NHL involve Ig or TCR gene sequences in combination with oncogene sequences. These chromosome aberrations do not give rise to fusion proteins, but result in increased or stabilized expression of the involved oncogene, thereby contributing to uncontrolled growth. They occur at relatively high frequency in particular disease categories, such as t(14;18) with involvement of the BCL2 gene in ~90% of follicular lymphomas and t(11;14) with involvement of the BCL1/Cyclin D1 gene in ~70% of mantle cell lymphomas.

From origin cytogenetic analysis of chromosomes has been the standard technique for detection of chromosome aberrations. This technique needs the presence of cells in metaphase, which generally requires various cell culture systems, dependent on the type of malignancy. The success rate for obtaining reliable karyograms is highly dependent on the type of malignancy and the experience of the laboratory and ranges from less than 50% to over 90%. Furthermore, some chromosome aberrations can not or hardly be detected by cytogenetic analysis such as TAL1 deletions in T-ALL and t(12;21) in precursor-B-ALL. Therefore in case of well-established chromosome aberrations the labor-intensive and time-consuming classical cytogenetics is now being replaced by molecular techniques. As the, molecular analysis of genetic aberrations can be performed with Southern blotting, polymerase chain reaction (PCR) techniques, and FISH techniques.

Southern blot analysis has long been the most reliable molecular method for detection of well-established chromosome aberrations, but this technique is dependent on the availability of suitable DNA probes, which recognize all relevant breakpoint cluster regions of the involved chromosome aberrations. The latter probably explains why BCL2 and BCL1/CyclinD1 gene aberrations are detectable by Southern blotting in only 75% of follicular lymphomas and in only 50% of mantle cell lymphomas, respectively. Furthermore, Southern blot analysis is time-consuming and requires relatively large amounts of high-quality DNA derived from fresh or frozen cell samples.

Over the last five years, PCR-based techniques have been developed as alternatives for Southern blotting. PCR techniques have the advantage that they are rapid and require minimal amounts of medium-quality DNA, which might even be obtained from formalin-fixed paraffin-embedded tissue samples. Also mRNA can be used after reverse transcription (RT) into cDNA. RT-PCR is especially valuable in case of chromosome aberrations with fusion genes and fusion transcripts, such as frequently seen in precursor-B-ALL and in t(2;5) in anaplastic large cell lymphoma. Despite these obvious advantages, the broad application of PCR techniques for detection of chromosome aberrations in hematopoictic malignancies is hampered by several problems. False-negative PCR results can be obtained if the DNA or mRNA from formalin fixed paraffin-embedded tissue samples is less optimal than anticipated, or when primers are mismatching. False-positive results might be obtained due to cross-contamination of PCR products between samples from different patients; especially in case of RT-PCR studies of fusion gene transcripts it might be difficult to exclude false-positive results. Finally, routine PCR analysis can only be used to study relatively small fussion regions of chromosome breakpoints (<2 kb). This implies that multiple oligonucleotide primer sets are needed to cover the most important breakpoint and fusion regions, whereas it will be difficult to study large breakpoint or fusion regions (>10 kb). This explains the lower detectability of chromosome aberrations, and thus again the presence of false-negative results, at the DNA level by PCR as compared to Southern blotting.

A major advantage of FISH techniques as compared to cytogenetic analysis, Southern blotting, and PCR analysis is that FISH can be performed on interphase nuclei of all kind of tissue and cell samples and that no need for extraction of DNA or mRNA exists. In FISH techniques generally, large DNA probes (>25 kb) are used, which are located around the breakpoint regions of the two chromosomes of the studied chromosome aberration. This implies that FISH probes can scan much larger regions than Southern blot probes or PCR primers. This advantage is especially important for detection of breakpoints outside the traditional breakpoint cluster regions. Furthermore the use of large fluorescently-labeled DNA probes allow direct and rapid visualization of deletions and translocations of the studied gene regions. Application of the latest generation of fluorescent microscopes with multiple fluorochrome filter combinations, CCD camera, and appropriate computer software allow the combined use of multiple FISH probes, which are labeled with different fluorochromes.

The availability of suitable probes is the main limiting factor in using FISH technology for detection of chromosome aberrations. Thus far, generally cosmid clones, YAC clones, or other cloned DNA fragments have been used without specific selection or modification of these probes. For many of these probes, the position in the genome is not precisely known; they often even overlap with breakpoint cluster regions, and they often contain repetitive sequences which cause high background staining. Furthermore, translocations are generally detected by use of two different probes, one for each of the involved chromosomes; these two probes are assumed to colocalize in case of a translocation, but show separate signals if no translocation is present. However, in practice, 2 to 4% of normal interphase cells will show false-positive results due to the fact that the two signals colocalize by chance.

For routine applicability of FISH techniques or other probe analysis assays or kits for the detection of chromosome aberrations in the diagnosis and classification of hematopoietic malignancies, it is necessary to design distinct and balanced probes.

The probes of the invention are selected to form a distinct and balanced pair of nucleic acid probes; size of the probes is each within certain limits of the genomes to be detected (e.g., 1–10, or 10–30, or 20–40, or 30–50, or 40–60 kb), with the final aim that the intensity fluorescent signals of the various probes is comparable.

In an additional embodiment of the invention, the position of the probes constituting the pair is determined precisely, i.e., no overlap with breakpoint cluster regions, the relevant breakpoints are preferably located within 50 kb or preferably even within 25 kb of either probe, and an additional probe pair has to be designed, if two breakpoint regions of a particular chromosome aberration are separated for more than 30–50 kb depending on the exact position of the probes.

In a further embodiment the nucleic acid probes do not contain (major) repetitive sequences, and do not cross-hybridize, which results in high background staining. For this reason the nucleic acid probes composed of several fragments can be tested either on metaphase spreads or with Southern blotting for hybridization sensitivity and specificity.

The nucleic acid probes can alternatively, or additionally be tested in fiber FISH prior to being employed in diagnostic testing, for mapping and checking their relative positions.

It has additionally been found that detection of chromosome breakpoints becomes easier and more reliable, if two separate probes, labelled with two different fluorochromes, constituting said pair are designed around one of the breakpoint regions of a chromosome aberration. This will lead to co-localization of the signals if no breakpoint is present. However if a breakpoint occurs in the studied breakpoint region, the two differently labeled probes will result in two separate signals.

In addition, the design of a third probe (labeled with a third fluorochrome) and thus the design of two additional distinct pairs of probes for the partner gene of the chromosome aberration allows precise identification of the chromosome aberration.

Chromosome aberrations found in malignancies are useful for molecular classification, such as in case of acute leukemias, malignant lymphomas and solid tumors (Table 1). However, several of these aberrations are more important than others, because of their high frequency or because of their prognostic value. For instance, t(14;18) occurs frequently in NHL, whereas t(12;21) is frequently found in childhood precursor-B-ALL. On the other hand, translocations involving the MLL gene in the 11q23 region represent a poor prognostic factor and the presence of 11q23 (MLL gene) aberrations is already in use as an important factor for stratification of treatment in acute leukemias. Also t(9;22) in ALL has a poor prognosis and is used for treatment stratification.

The MLL (for myeloid-lymphoid leukemia or mixed-lineage leukemia) gene in chromosome region 11q23 is involved in several translocations in both ALL and acute myeloid leukemias (AML). In these translocations the MLL gene, encoding a protein that shows homology to the Drosophila trithorax gene product, is fused to partner genes on different chromosomes. To date, at least ten partner genes have been identified. Some of these translocations, like the t(4;11) (q21;q23), t(11;19) (q23;p13) and t(1;11) (p32;q23), predominantly occur in ALL, where as others, like t(1;11) (q21;q23), t(2;11) (p21;q23), t(6;11) (q27;q23) and t(9;11) (p22;q23) are more often observed in AML. Other types have been reported in ALL as well as AML. Treatment-induced AML with 11q23 aberrations can arise in patients previously treated with topoisomerase II inhibitors. Rearrangements involving the 11q23 region occur very frequently in infant acute leukemias (around 60–70%), and to a much lesser extent in childhood and adult leukemias (each around 5%). MLL gene rearrangements, especially the t(4;11), have been shown to be a poor prognostic factor in infant leukemias, resulting in a 3-year overall survival of 5% as compared to 85–90% in cases with germline MLL genes.

The large MLL gene (>100 kb) consists of 21 exons, encoding over 3900 amino acids. Breakpoints in the MLL gene are clustered in a 8.5–9 kb region that encompasses exons 5–11. Because of its relatively small size, this breakpoint region is easily accessible for molecular detection of translocations. By choosing two distinctly-labeled FISH probes in the sequences flanking the breakpoint region, any translocation involving the 11q23 region can be detected on the basis of segregation of the two fluorochrome signals, whereas the two fluorochromes colocalize when no rearrangement in the MLL gene has occurred. Furthermore, the use of a third fluorochrome for probes directed against partner genes enables the identification of the precise type of translocation. This two-step approach of FISH analysis guarantees efficient and direct detection of all aberrations involving the 11q23 (MLL gene) region in the first step, whereas in the second step the type of 11q23 translocation can be determined.

Chromosome aberrations in lymphoid malignancies often involve Ig or TCR genes. Examples include the three types of translocations (t(8;14), t(2;8), and t(8;22)) that are found in Burkitt's lymphomas, in which the MYC gene is coupled to Ig heavy chain (IGH), Ig kappa (IGK), or Ig lambda (IGL) gene segments, respectively. Another common type of translocation in this category is the t(14;18) (q32;q21) that is observed in ~90% of follicular lymphomas, one of the major NHL types. In this translocation the BCL2 gene is rearranged to regions within the IGH locus within or adjacent to the JH gene segments. The result of this chromosome aberration is the overexpression of the BCL2 protein, which plays a role as survival factor in growth control by inhibiting programmed cell death.

The BCL2 gene consists of only three exons, but these are scattered over a large area. Of these the last exon encodes a large 3' untranslated region (3' UTR). This 3' UTR is one of the two regions in which many of the t(14;18) breakpoints are clustered and is called "major breakpoint regions" (mbr); the other breakpoint region involved in t(14;18) translocations, is located 20–30 kb downstream of the BCL2 locus and is called the "minor cluster region" (mcr). A third BCL2 breakpoint area, the vcr (variant cluster region), is located at the 5' side of the BCL2 locus and is amongst others involved in variant translocations, i.e., t(2;18) and t(18;22), in which IGK and IGL gene segments are the partner genes.

By choosing a set of FISH probes that are located in the regions upstream of the mbr region and downstream of the mcr region, translocations in these regions can be detected upon segregation of the fluorochrome signals. An additional set of FISH probes is designed for the vcr region, since the distance between the vcr region and the other two breakpoint clusters is far too large (~400 kb) to use the same probes. As a second step in all these approaches, FISH probes in the IGH, IGK, and IGL genes are used for identification of the exact type of translocation.

Several types of nucleic acid probes can be employed in FISH technology as provided by the invention for detection of chromosome aberrations. Each of these probe types has its own characteristic features and advantages, together constituting a complementary approach, i.e., cosmid, PAC, or YAC derived probes, PCR-based probes, or PNA-based probes.

Clones obtained from cosmid, PAC or YAC libraries constitute large probes that, when labeled with fluorochromes, result in appropriate signals upon hybridization (Gingrich et al., 1996). However, conventionally as the precise position of these probes is unknown, there often is a risk of overlap with the breakpoint cluster region of the involved chromosome aberration, if no further selection or modification of these probes is performed. Furthermore, such large probes often contain repetitive sequences, which cause high background staining. Distinct and balanced pairs of probes comprising cosmid, PAC or YAC probes that are designed to react with the flanking regions upstream and downstream of the breakpoint area on one of the involved chromosomes can therefore be exactly positioned in fiber FISH experiments or by use of Southern blotting using small well-defined inclusion and exclusion probes which are designed around the breakpoint area avoiding said overlap with the breakpoint cluster. The presence of potential repetitive sequences is excluded via Southern blot analysis of genomic DNA.

Probes that are generated by PCR-have the additional advantage that they can be positioned exactly, however for this approach sequence information is required at least in the areas for designing the target-specific PCR primers for producing the probes. Once generated the PCR products are checked for the presence of repetitive or cross-hybridizing sequences that hamper specific detection of the flanking regions upstream and downstream of the involved break point cluster. PNA-based probes for FISH technology comprise multiple (e.g., 50–150) distinct PNA oligonucleotides each of which shows a typical size of 5–40, more typically 10–25 nucleotides and which together produce an appropriate signal for detection of chromosome aberrations using FISH technology. PNA probes, having a neutral peptide backbone to which the four deoxynucleotides are coupled are stable nucleic acid fragments that hybridize to complementary nucleic acid sequences with high affinity (Egholm et al., 1993; Corey, 1997). Due to the fact that mismatches strongly influence PNA hybridization, sequence specificity of PNA recognition can be easily achieved, thereby rendering PNA probes highly selective probes to be used in FISH technology. PNA probes have now been used in a variety of applications including in situ hybridization to highly repetitive contromeric or telomeric sequences (Corey, 1997). Thus far, only a single PNA oligonucleotide directed against repeated sequences was sufficient for appropriate signal intensities. The design of a balance pair of nucleic acid probes comprising multiple (e.g., 50–150) distinct PNA oligonucleotides directed against target sequences in the flanking regions of a breakpoint cluster provides detection of chromosome aberrations as well as with other nucleic acid probes.

Applicability of the Various Types of Probes

Each of the previously herein mentioned types of FISH probes has its specific applicability, but together they constitute complementary and partly overlapping strategies.

The MLL gene in chromosome region 11q23 is an example of a detectable region that is involved in several translocations in both ALL and AML (Table 1), providing a perfect example of a chromosome aberration for which PCR-based or PNA-based FISH probes can preferably be designed. Because the breakpoint area in the MLL gene is so tightly clustered with ample exons available in the flanking regions upstream and downstream of the breakpoint cluster, sequence-based design and production of distinct and balanced pairs of PCR-based and/or PNA-based FISH probes is very useful in this chromosome region. Design of precisely positioned cosmid or PAC clones could be useful as an alternative or additional strategy.

The BCL2 gene area is an example that is involved in several chromosome aberrations in malignant lymphomas (Table 1) which contains several breakpoint areas which are located outside the coding sequence at the 5' and 3' sides of the BCL2 locus and which are lying far apart. The BCL2 locus therefore exemplifies a gene involved in chromosome aberrations for which distinct and balanced pairs of FISH probes are more difficult to generate via PCR and/or via pooling of PNA oligonucleotides, as less sequence information is available. In such chromosome aberrations distinct and balanced pairs of cosmid, PAC, and/or YAC derived FISH probes can be employed after careful selection and modification of the exact position.

Although the invention has been explained with reference to certain specific details and illustrative examples, the scope of the invention is to be determined by the appended claims.

REFERENCES

1. Gingrich J. C., Boehrer D, Garnes J. A., Johnson W., Wong B., Bermann A., Eveleth G. G., Longlois R. G., Carrano A. V. Construction and characterization of human chromosome 2-specific cosmid, fosmid, and PAC clone libraries. *Genomics* 1996;32:65–74.
2. Egholm M., Buchard O., Christensen L., Behrens C., Freier S. M., Driver S. A., Berg R. H., Kim S. K., Noreden B., Nielsen P. E. PNA hybridizes to complementary oligonucleotides obeying the Watson-Crick hydrogen-bonding rules. *Nature* 1993;365:566–568
3. Corey D. R. Peptide nucleic acids: expanding the scope of nucleic acid recognition. *Tibtech* 1997;15:244–229.
4. Wiegant J., Kalle W., Mullenders L., Brookes S., Hoovers J. M. N., Dauwerse J. G., Van Ommen G. J. B., Raap A. K. High-resolution in situ hybridization using DNA halo preparations. *Hum. Mol. Genet* 1992:5:17–21
5. Young B. D., Saha V. Chromosome Abnormalities in Leukaemia: The 11q23 Paradigm Cancers Surveys 1996;28:225–245
6. Nilson I., Löchner K., Siegel G., Griel J., Beck J. D., Fey G. H., Marschalek R. Exon/ingron structure of the human ALL-1 (MLL) gene involved in translocations to chromosomal region 11q23 and acute leukaemias. *Br J Haematol* 1996;93:966–972
7. Taki T., Ida K., Bessho F., Hanada R., Kikuchi A., Yamamoto K., Sako M., Tsuchida M., Seto M., Ueda R., Hayashi Y. Frequency and clinical significance of the MLL gene rearrangements in infant acute leukemia. *Leukemia* 1996;10:1303–1307
8. Gascoyne R. D., Adomat S. A., Krajewski S., Kajewska M., Horsman A., Tolcher A. W., O'Reilly S. E., Hoskins, Coldman A. J., Reed J. C., Connors J. M. Prognostic significance of Bcl-2 protein expression and Bcl2-gene rearrangement in diffuse aggressive Non-Hodgkin's lymphoma. *Blood* 1997,90:244–251
9. Seto M.,Jaeger U., Hockett R. D., Graninger W., Benett S., Goldman P., Korsmeyer S. J. Alternative promoters and exons, somatic mutation and deregulation of the BCL2-lg fusion gene in lymphoma. *EMBO J* 1988;7:123–131
10. Seite P., Leroux D., Hillion J., Monteil M., Berger R, Mathieu-Mahul D., Larsen C. J. Molecular analysis of a variant 18;22 translocation in a case of lymphocytic lymphoma. *Genes Chrom Cancer* 1993;6:39–44
11. Tashiro S., Takechi M., Asou H., Takauchi K, Kyo T., Dohy H., Kikuchi M., Kamada N., Tsjujimoto Y. Cytogenetic 2;18 and 18;22 translocation in chronic lymphocytic leukemia with juxtaposition of bcl-2 and immunoglobulin light chain genes. *Oncogene* 1992;7:573–577
12. Hibshoosh H., Lattes R. Immunohistochemical and molecular genetic approaches to soft tissue tumor diagnosis; a primer. *Semin Oncol* 1997;24:515–525
13. Zoubek A., Dockhom-Dworniczak B., Delattere O., Christiansen H., Niggli F., Gatterer-Menz I., Smith T. L., Jürgens H., Gadner H., Kovar H. Does expression of different EWS chimeric transcripts define clinically distinct risk groups of Ewing tumor patients? *J Clin Oncology* 1996;14:1245–1251

TABLE 1

Examples of chromosome aberrations in malignancies, that are detectable with a distinct and balanced pair of nucleic acid probes of the invention.

| Translocation | Involved genes | Primary target gene for FISH probe design | Occurrence per disease category |
|---|---|---|---|
| Acute leukemias | | | |
| t(4;11) (q21;Q23) | MLL-AF4 | MLL gene | 70% of infant ALL |
| t(11;19) (q23;p13) | MLL-ENL | | 5–7% of ALL |
| t(6;11) (q27;q23) | MLL-AF6 | | 5–6% of AML |
| t(9;11) (p22;q23) | MLL-AF9 | | |
| Malignant lymphomas | | | |
| t(14;18) (q23;q21) | BCL2-IGH | BCL2 gene | 90% of follicular NHL |
| t(2;18) (q12;q21) | IGK-BCL2 | | 25% of immunoblastic NHL |
| t(18;22) (q21;q11) | IGL-BCL2 | | 25% of diffuse large cell centroblastic NHL 5–10% of B-CLL |

TABLE 1-continued

Examples of chromosome aberrations in malignancies, that are detectable with a distinct and balanced pair of nucleic acid probes of the invention.

| Translocation | Involved genes | Primary target gene for FISH probe design | Occurrence per disease category |
|---|---|---|---|
| Solid tumors | | | |
| t(11;22) (q24;q12) | EWS-FLI1 | EWS gene | >95% of Ewing sarcoma |
| t(21;22) (q22;q12) | EWS-ERG | | |
| t(7;22) (p22;q12) | EWS-ETV1 | | |

What is claimed is:

1. A method of detecting a acid molecule having a chromosomal aberration, said method comprising:
   providing a pair of nucleic acid probes to detect chromosomal aberrations in hematological malignancies and to analyze a sample believed to contain said nucleic acid, said pair of nucleic acid probes having comparable size, said size being selected from the group consisting of 1 to 100 kb, 1 to 10 kb, 7 to 15 kb, 10 to 20 kb, 10 to 30 kb, 20 to 40 kb, 30 to 50 kb, 40 to 60 kb, 50 to 70 kb, 60 to 80 kb, 70 to 90 kb and 80 to 100 kb, and said pair of nucleic acid probes flanking a potential breakpoint in a single chromosome, each of said pair of nucleic acid probes being labeled with at least one different reporter molecule;
   hybridizing said pair of nucleic acid probes to said nucleic acid; and
   detecting the presence of a split signal that arises after a break within said potential breakpoint in the case of chromosomal aberration.

2. A method of detecting cells suspected of having a chromosomal aberration, said method comprisng:
   providing a pair of nucleic acid probes to detect chromosomal aberrations in hematological malignancies and to analyze nucleic acid of said cells, said pair of nucleic acid probes having comparable size, said size being selected from the group consisting of 1 to 100 kb, 1 to 10 kb, 7 to 15 kb, 10 to 20 kb, 10 to 30 kb, 20 to 40 kb, 30 to 50 kb, 40 to 60 kb, 50 to 70 kb, 60 to 80 kb, 70 to 90 kb and 80 to 100 kb, and said pair of nucleic acid probes flanking a potential breakpoint in a single chromosome, each of said pair of nucleic acid probes being labeled with at least one different reporter molecule;
   hydridizing said pair of nucleic acid probes to the nucleic acid of at least one of said cells; and
   detecting the presence of a split signal that arises after a break within said potential breakpoint in the case of a chromosomal aberration.

3. A method of detecting a break within a potential breakpoint of a single chromosome, said method comprising:
   associating a pair of nucleic acid probes for detection of chromosome aberrations in
   hematological malignancies and a sample believed to contain nucleic acid complimentary to said pair of nucleic acid probes, said pair of nucleic acid probes having comparable size, said size being selected from the group consisiting of 1 to 100 kb, 1 to 10 kb, 7 to 15 kb, 10 to 20 kb, 10 to 30 kb, 20 to 40 kb, 30 to 50 kb, 40 to 60 kb, 50 to 70 kb, 60 to 80 kb, 70 to 90 kb and 80 to 100 kb, each nucleic acid probe of said pair of nucleic acid probes being labeled with at least one different reporter molecule and flanking a potential breakpoint in said single chromosome;
   hybridizing said pair of nucleic acid probes to said nucleic acid; and
   determining whether a split-signal that arises after a break within said potential breakpoint in the case of chromosomal aberrations is present in said sample.

4. The method according to claim 3, which pair of nucleic acid probes hybridize to a nucleic acid molecule at a genomic distance of from about 50 kb to no more than 100 kb.

5. The method according to claim 3, wherein the at least one reporter molecule of said at least one different report molecule is selected from the group consisting of enzymes, chromophores, fluorochromes, and haptens.

6. The method according to claim 5, wherein the pair of nucleic acid probes hybridize to a single corresponding nucleic acid molecule.

7. The method according to claim 6, wherein the single corresponding nucleic acid molecule is at least a fragment of a chromosome.

8. The method according to claim 7, wherein the choromosome is not aberrant.

9. The method according to claim 3, which hybridize in situ.

10. The method according to claim 9, which pair of nucleic acid probes each hybridize in situ to only a few linear DNA molecules per cell.

* * * * *